(12) United States Patent
Yi et al.

(10) Patent No.: US 10,039,852 B2
(45) Date of Patent: Aug. 7, 2018

(54) AIR PURIFIER USING ULTRAVIOLET RAYS

(71) Applicant: Seoul Viosys Co., Ltd., Ansan-si (KR)

(72) Inventors: Jae Seon Yi, Ansan-si (KR); Young Hwan Son, Ansan-si (KR); Seong Min Lee, Ansan-si (KR); Jong Rack Kim, Ansan-si (KR); Ik Hwan Ko, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 273 days.

(21) Appl. No.: 14/478,948

(22) Filed: Sep. 5, 2014

(65) Prior Publication Data

US 2015/0064069 A1    Mar. 5, 2015

(30) Foreign Application Priority Data

Sep. 5, 2013  (KR) .................. 10-2013-0106883
Sep. 5, 2013  (KR) .................. 10-2013-0106884

(51) Int. Cl.
*A61L 9/20*    (2006.01)
*B01D 46/00*   (2006.01)
*F24F 1/00*    (2011.01)
*F24F 3/16*    (2006.01)

(52) U.S. Cl.
CPC ............. *A61L 9/20* (2013.01); *A61L 9/205* (2013.01); *B01D 46/0028* (2013.01); *A61L 2209/11* (2013.01); *A61L 2209/14* (2013.01); *F24F 2001/0096* (2013.01); *F24F 2003/1667* (2013.01)

(58) Field of Classification Search
CPC ........ A61L 9/20; A61L 9/205; B01D 46/0028
See application file for complete search history.

(56) References Cited

U.S. PATENT DOCUMENTS

| | | | | |
|---|---|---|---|---|
| 5,601,786 A | * | 2/1997 | Monagan | A61L 9/20 250/437 |
| 5,656,242 A | * | 8/1997 | Morrow | A61L 9/20 422/120 |
| 5,835,840 A | * | 11/1998 | Goswami | A61L 9/20 422/186.3 |
| 5,919,422 A | * | 7/1999 | Yamanaka | A61L 2/232 422/121 |
| 5,997,619 A | * | 12/1999 | Knuth | A61L 9/20 55/356 |
| 6,264,888 B1 | * | 7/2001 | Palestro | A61L 9/20 422/24 |
| 6,497,840 B1 | * | 12/2002 | Palestro | A61L 9/20 250/432 R |
| 6,500,387 B1 | * | 12/2002 | Bigelow | A61L 9/20 250/432 R |
| 6,666,912 B1 | * | 12/2003 | Yan | A61L 9/20 55/472 |

(Continued)

FOREIGN PATENT DOCUMENTS

| | | | |
|---|---|---|---|
| CA | 2150320 A1 | * 11/1996 | ............... A61L 9/20 |
| KR | 1020110057562 A | 6/2011 | |
| KR | 1020110096258 A | 8/2011 | |

*Primary Examiner* — Regina M Yoo

(74) *Attorney, Agent, or Firm* — Perkins Coie LLP

(57) ABSTRACT

An air purifier includes a case having an air inlet and an air outlet, a fan disposed adjacent the air inlet, a UV LED unit and a filter unit arranged over the fan along a flow path of air, and a fluid control structure disposed between the fan and the filter unit.

18 Claims, 17 Drawing Sheets

(56) References Cited

U.S. PATENT DOCUMENTS

| | | | | |
|---|---|---|---|---|
| 7,089,763 B2* | 8/2006 | Forsberg | | E03B 3/28 62/285 |
| 7,364,605 B2* | 4/2008 | Yuen | | A61L 9/20 422/121 |
| 8,017,073 B2* | 9/2011 | Engelhard | | A61L 9/205 422/24 |
| 2001/0043887 A1* | 11/2001 | Morneault | | A61L 9/20 422/121 |
| 2001/0048889 A1* | 12/2001 | Palestro | | A61L 9/20 422/4 |
| 2003/0024254 A1* | 2/2003 | Yoshida | | F25D 17/042 62/78 |
| 2003/0206841 A1* | 11/2003 | Lopiccolo | | A61L 9/20 422/307 |
| 2005/0000365 A1* | 1/2005 | Nelsen | | A61L 9/16 96/224 |
| 2005/0265890 A1* | 12/2005 | Yang | | D06F 58/20 422/5 |
| 2006/0177356 A1* | 8/2006 | Miller | | A61L 9/16 422/121 |
| 2007/0163588 A1* | 7/2007 | Hebrank | | A61L 9/16 128/204.18 |
| 2007/0253860 A1* | 11/2007 | Schroder | | A61L 9/015 422/4 |
| 2008/0245092 A1* | 10/2008 | Forsberg | | E03B 3/28 62/288 |
| 2011/0030560 A1* | 2/2011 | Bohlen | | A61L 9/015 96/57 |
| 2011/0033346 A1* | 2/2011 | Bohlen | | A61L 9/205 422/186.3 |
| 2011/0232481 A1* | 9/2011 | Worrilow | | A61L 9/20 95/10 |
| 2012/0199003 A1* | 8/2012 | Melikov | | A61G 10/02 95/273 |
| 2012/0283508 A1* | 11/2012 | Worrilow | | A61L 9/20 600/33 |
| 2013/0017135 A1* | 1/2013 | Anderson | | B01D 45/12 423/210 |
| 2014/0020686 A1* | 1/2014 | Kristensson | | A61G 13/108 128/204.16 |
| 2014/0157989 A1* | 6/2014 | Kirschman | | B01D 46/0028 96/224 |
| 2015/0044101 A1* | 2/2015 | Koo | | F24F 3/1603 422/121 |
| 2015/0064061 A1* | 3/2015 | Taghipour | | A61L 9/205 422/4 |

* cited by examiner

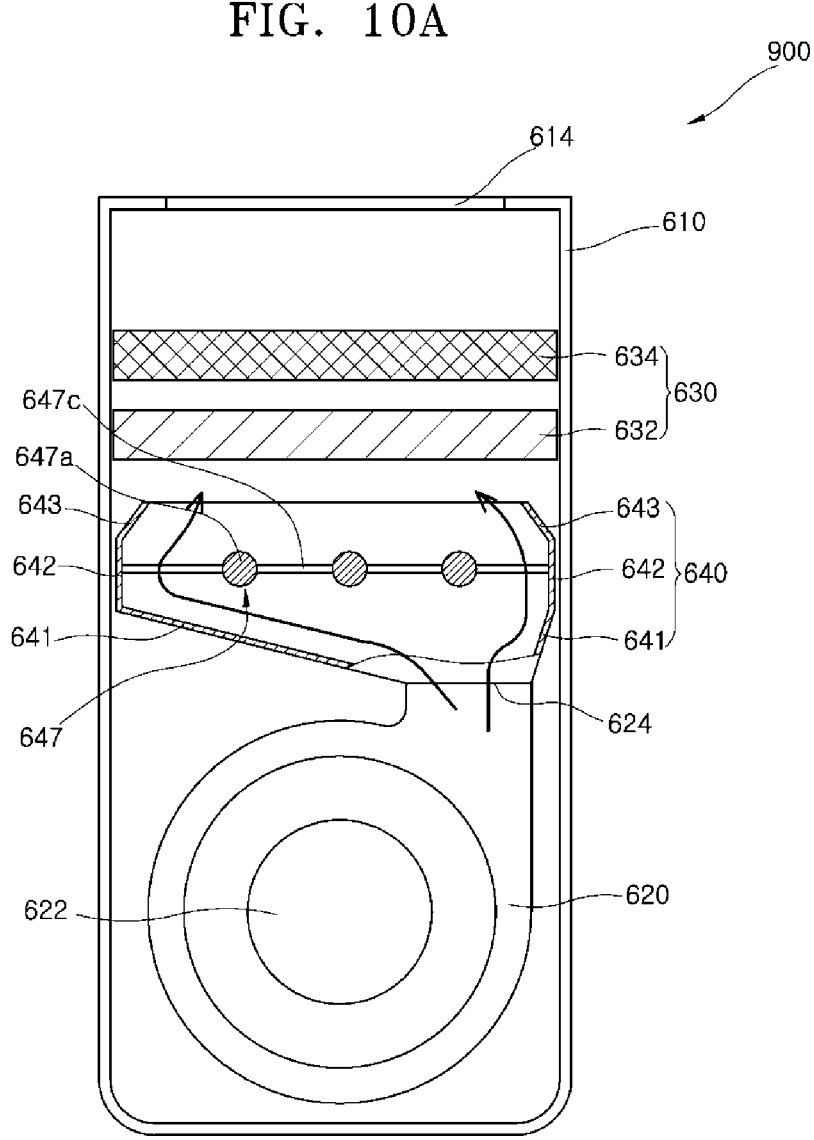

AIR PURIFIER USING ULTRAVIOLET RAYS

CROSS-REFERENCES TO RELATED APPLICATIONS

The present application claims priority to Korean application numbers 10-2013-0106883, and 10-2013-0106884, both filed on Sep. 5, 2013, the contents which are incorporated by reference in their entirety.

BACKGROUND

The disclosure of this patent document relates to a technology for an air purifier including an air purifier using ultraviolet (UV) rays.

Recently, the quality of air in Korea has been rapidly degraded. For example, air contaminants caused by the rapid industrialization of China cover the Korean peninsula with yellow dust. Thus, the concentration of air contaminants including harmful heavy metals in the air of Korea has exceeded to a worrying degree. Furthermore, the quality of indoor air in many buildings has been degraded by air contaminants such as fine dust, formaldehyde, and airborne bacteria. Thus, a lot of people have been said to suffer from the sick building syndromes with symptoms such as sneeze, cough, fatigue, and dry and sore nose, eyes, and throat.

Such environmental conditions are or can be some of the factors increasing the demand for an air purifier capable of purifying contaminated air. Most of air purifiers which are currently used in common include or can include various filters provided with the air purifiers, and receive the contaminated air and purify the contaminated air by physically filtering or adsorption-filtering contaminant particles through the filters.

Recently, there has been proposed a method which directly sterilizes the air using UV rays or purifies the air through radicals generated by reactions between a photocatalyst filter and UV rays. An example of such an air purification method using UV rays has been disclosed in Korean Patent Laid-open Publication No. 2011-0096258.

Fans used in air purifiers may be classified into axial-type fans and centrifugal fans. The axial-type fans generate air flow in the direction parallel to the rotation axis of an impeller, and a domestic fan may be taken as an example of the axial-type fans. The centrifugal fans may take air flow in the direction of the rotation axis thereof, but discharge air flow in the direction perpendicular to the rotation axis thereof, and a blower fan may be taken as an example of the centrifugal fans. An example of the technique related to the air purifier employing the centrifugal fan has been disclosed in Korean Patent Laid-open Publication No. 2011-0057562.

SUMMARY

In one embodiment, an air purifier includes a case having an air inlet and an air outlet, a fan disposed inside the case and adjacent the air inlet, an ultraviolet (UV) light emitting diode (LED) unit and a filter unit arranged inside the case over the fan along a flow path of air, and a fluid control structure disposed inside the case between the fan and the filter unit. The fluid control structure controls an air flow along the flow path of air between an outlet of the fan and the filter unit.

In another embodiment, an air purifier includes a case having an air inlet and an air outlet, and an air purification unit disposed along a flow path of air within the case. The air purification unit includes a printed circuit board (PCB) having through-holes formed on the PCB, UV LEDs arranged on the PCB, and a light reflecting structure disposed to surround the UV LEDs. The air flows along the flow path within the case and through the through-holes and UV LEDs irradiate UV rays onto the air that passes through the through-holes to sterilize the air.

In another embodiment, an air purifier includes a case having an air inlet and an air outlet, a fan disposed inside the case and adjacent to the air inlet, a filter unit arranged inside the case and over the fan along a flow path of air leading to the air outlet, the filter unit operable filter the air flow, an ultraviolet (UV) unit inside the case to direct UV light to a location in the flow path of air, causing sterilization of the air flow, a fluid control structure disposed inside the case between the fan and the filter unit, and a light reflecting structure disposed inside the case to surround the UV LED unit to spread the UV light irradiated to the filter unit.

BRIEF DESCRIPTION OF THE DRAWINGS

FIG. 10A is a schematic cross-sectional view of an exemplary air purifier in accordance with a sixth embodiment of the disclosed technology.

DESCRIPTION OF SPECIFIC EMBODIMENTS

Figure 1:
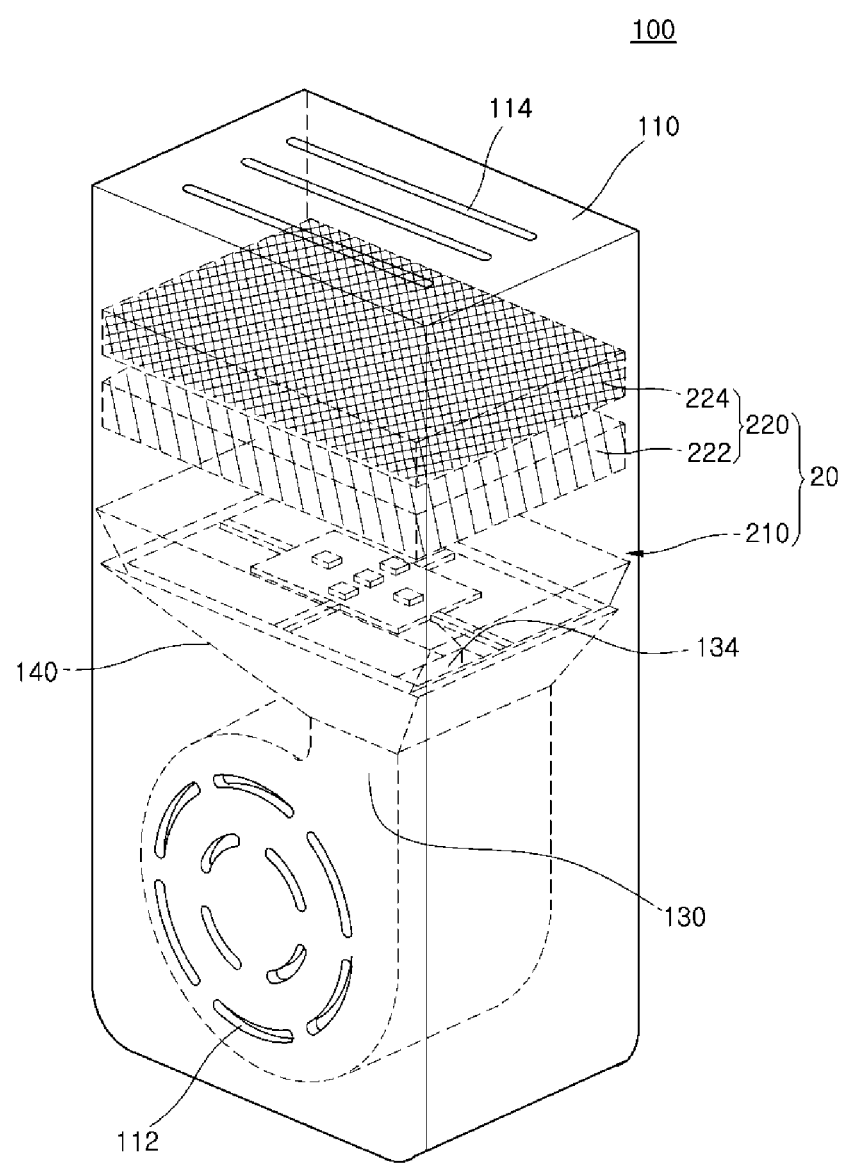
FIG. 1 schematically illustrates an exemplary air purifier in accordance with a first embodiment of the disclosed technology.

Embodiments of the disclosed technology on air purifiers will hereinafter be described in detail with reference to the accompanying drawings. It should be noted that the drawings are not to precise scale and may be exaggerated in some aspects, e.g. in thickness of lines or sizes of certain components for descriptive convenience and clarity only.

In embodiments of the disclosed technology, the term such as 'first' or 'second' can be used to distinguish between members, but does not limit a specific member or indicate a specific order. Furthermore, when an element is referred to as being positioned on another element or 'over', 'under', and 'by' another element, the element can indicate the relative positional relationship between the elements. Thus, the former element may be directly contacted with the latter element, or an additional element may be interposed at the interface between the elements. Furthermore, when an element is referred to as being 'coupled' or 'connected' to another element, it may indicate that the former element is directly coupled or connected to the latter element or an additional element is interposed therebetween. Throughout the specification, like reference numerals denote substantially the same components.

Figure 2:
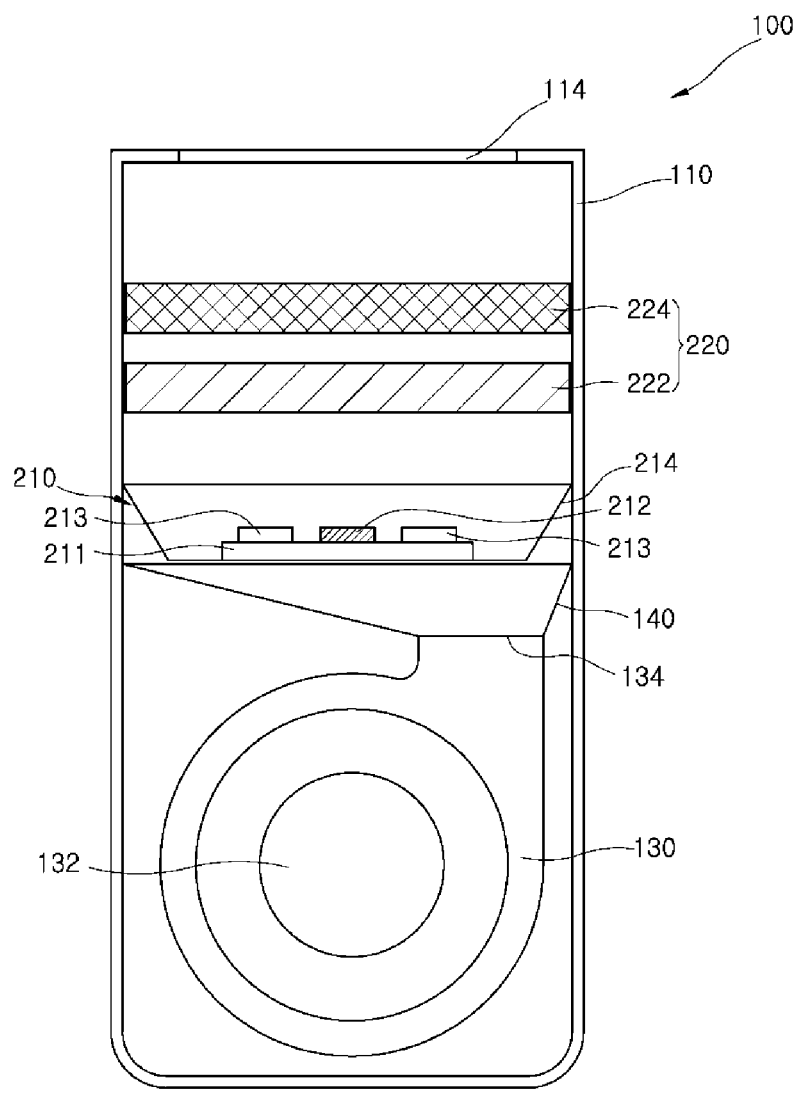
FIG. 2 is a schematic cross-sectional view of the air purifier of FIG. 1.

FIG. 1 schematically illustrates an air purifier in accordance with a first embodiment of the present disclosure. FIG. 2 is a schematic cross-sectional view of the air purifier of FIG. 1. Referring to FIGS. 1 and 2, the air purifier 100 can include a case 110 and an air purification unit 20. The air purification unit 20 can include a UV light source 210 and a filter unit 220. The UV light source 210 is provided as part of the air sterilization mechanism that is built into the device. Examples below provide two different UV emissions at two different UV spectral ranges for two different UV-based air sterilization processes.

The case 110 can include an air inlet 112 and an air outlet 114, and form a body part of the air purifier 100. Referring to the drawings in FIGS. 1 and 2, an available volume of space representing an air flow path from a top of the UV light source 210 upward to the air outlet 114 created by arrangements of internal structures of the case 110 can have substantially the same cross-sectional area throughout the air flow path. In other embodiments, however, cross-sectional areas formed along the air flow path may be different from each other or at various points of the air flow path, and modified or can be modified in various manners.

In the case 110 adjacent to the air inlet 112, a fan 130 can be disposed to be substantially aligned with the inlet 112 to expedite flow of air introduced into the case 110. The fan 130 can include a blower fan or axial-type fan, for example. FIGS. 1 and 2 illustrate a blower fan, for example, but the fan 130 is not limited to a blower fan. The fan 130 can include an inlet 132 adjacent to and substantially aligned with the air inlet 112 to expedite the entry of the air into the case. The fan 130 can include an outlet 134 for discharging introduced air towards a fluid control structure or an air duct 140.

When a blower fan is applied or used as the fan 130 as illustrated in the drawings of FIGS. 1 and 2, the outlet 134 of the fan 130 can have a smaller cross-sectional area than the cross-sectional area of the case 110. In this case, the air discharged from the outlet 134 of the fan 130 can stay around or near the outlet 134 or flow toward a bottom of the case 110. Thus, as illustrated in the drawings of FIGS. 1 and 2, a fluid control structure or an air duct 140 can be disposed to couple with and extend from the outlet 134 of the fan 130 toward an inner wall of the case 110. Thus, the air discharged from the outlet 134 of the fan 130 can uniformly or substantially uniformly flow to an internal space of the case 110 feeding the air purification unit 20. As illustrated in the drawings of FIGS. 1 and 2, the fluid control structure or air duct 140 can include an air duct for controlling air flow. The fluid control structure or air duct 140 can be not only disposed to extend from the outlet 134 of the fan 130 toward the inner wall of the case 110, but also can be disposed at a proper position between the air inlet 112 and the air purification unit 20 to provide substantially uniform flow of air discharged from the outlet of the fan 130 towards the air purification unit 20.

The air purification unit 20 can be disposed over the fan 130 to receive and purify air discharged from the outlet 134 of the fan 130. As illustrated in the drawings of FIGS. 1 and 2, the UV light source 210 and the filter unit 220 can be sequentially disposed to have the filter unit 220 above the UV light source 210.

The UV light source 210 can include a printed circuit board (PCB) 211 with UV LEDs 212 and 213 that emit UV light at different UV spectral ranges and are arranged on the PCB 211, and a light reflecting structure 214. The PCB 211 can have through-holes formed on the PCB, through which air is passed. The light reflecting structure 214 can be disposed to surround the UV LEDs 212 and 213, and reflect UV rays emitted from the UV LEDs 212 and 213 so as to increase a frequency at which air flowing through the through-holes and along the flow path comes in contact with the emitted UV rays. In one aspect, the light reflecting structure 214 can be disposed at the sides of the UV LEDs 212 and 213 so as to have a larger height than the UV LEDs 212 and 213 with a reflecting surface of the reflecting structure facing the sides of the UV LEDs 212 and 213 at a predetermined angle with respect to the PCB 211. For example, the light reflecting structure 214 can be extended toward the inner wall of the case 110 as the height of the light reflecting structure 214 is increased in such a way that a base of the light reflecting structure 214 is further away from the inner wall of the case 110 than a top of the light reflecting structure 214. In other embodiments, the PCB 211 can be disposed in or integrated with the light reflecting structure 214.

The UV LEDs 212 and 213 can emit UV rays to the air having passed through the through-holes to cause UV-based sterilization of the air in two different ways. The UV LEDs 212 are sterilization UV LEDs 212, for example, that emit UV light that is sufficient to directly sterilize the air. THE UV LEDs 213 are photocatalyst UV LEDs 213, for example, that emit UV light at longer UV wavelengths for causing photocatalyst reaction in a photocatalyst material to cause sterilization of the air. The arrangement of the sterilization UV LEDs 212 and photocatalyst UV LEDs 213 on the PCB can be varied to have different configurations depending on the specific needs or design considerations. The UV LEDs 212 and 213 can be arranged in such a manner that the flow direction of the air flowing along the air flow path coincides with the irradiation direction of the UV rays. For example, the air can flow from the bottom of the case 110 toward the top of the case 110, and the UV LEDs 212 and 213 can be arranged on the PCB 211 so as to irradiate UV rays toward the top of the case 110.

In some implementations, the sterilization UV LEDs 212 can emit UV rays with a wavelength range 200 nm to 300 nm, and the photocatalyst UV LEDs 213 can emit UV rays with a wavelength range of 300 nm to 400 nm, longer than the UV rays by the wavelengths of sterilization UV LEDs 212.

The filter unit 220 can be disposed over the UV light source 210 so as to face or substantially face the UV LEDs 212 and 213. For example, the filter unit 220 can include a photocatalyst filter 222 and a collection filter 224 which are sequentially positioned over the UV LEDs 212 and 213 with the collection filter 224 disposed over the photocatalyst filter 222.

The photocatalyst filter 222 can include a material for providing a photocatalytic reaction under UV illumination, as a photocatalyst medium. For example, the photocatalyst medium can include but is not limited to titanium oxide ($TiO_2$), zinc oxide (ZnO), tungsten oxide ($WO_3$), or zirconium oxide ($ZrO_2$). The photocatalyst filter 222 can have a layered-structure including $TiO_2$ as at least one of the layers of the layered-structure. The photocatalyst filter 222 can be formed of a layer or layers obtained by coating a material such as metal foam or porous metal, through which air flow can be passed.

The photocatalyst filter 222 can cause a photocatalytic reaction with UV rays with a wavelength of 300 nm to 400 nm, emitted from the UV LEDs 213. When the UV rays are absorbed into the photocatalyst medium, electrons (e−) and holes (+) are formed at a surface of the photocatalyst medium, and the photocatalyst medium induced electrons can react with oxygen existing at the surface of the photocatalyst medium so as to generate superoxide negative ions ($O^{2-}$). Furthermore, the photocatalyst medium induced holes can react with moisture existing in the air so as to generate hydroxyl radicals (OH—.). The hydroxyl radicals generated at this time responsive to the reaction between photocatalyst medium induced holes and moister in the air can oxidize and decompose organic materials in the air flowing through the air flow path and through the photocatalyst filter 222. Thus, organic materials such as contaminants and malodorous substances within the air introduced into the air purifier can be decomposed into water and carbon dioxide. Furthermore, the hydroxyl radicals can serve as a strong oxidizing agent to perform sterilization. Thus, the photocatalyst filter 222 can deodorize and sterilize the introduced air flowing through the air flow path in cooperation with the photocatalyst UV LEDs 213.

The collection filter 224 can perform a function of collecting bacteria within the introduced air that flow through the air flow path and through the collection filter 224. For this operation, the collection filter 224 can have minute holes through which bacteria cannot easily pass. The collection filter 224 can include a filter material which has a shape bent with respect to the air flow direction, in order to increase a surface area of the collection filter 224 and improve the amount of bacteria collected per unit area. The bacteria collected in the collection filter 224 can be sterilized by UV rays with a wavelength of 200 nm to 300 nm, emitted from the sterilization UV LEDs 212. The collection filter 224 can increase the time during which the bacteria within the air flowing through the air flow path are exposed to the sterilization UV rays, thereby improving the sterilization efficiency of the sterilization UV LEDs 212. In other embodiments, the collection filter 224 can include a sterilization agent. The sterilization agent can additionally increase the sterilization efficiency.

In other embodiments, the air purifier 100 can further include a carbon filter. The carbon filter can be disposed between the fan 130 and the UV light source 210 or next to the filter unit 220 before or below the photocatalyst filter 222 and collection filter 224. The carbon filter can include active carbon and catalyst to filter out or remove organic chemical materials within the air. Thus, the carbon filter can deodorize the introduced air flowing through the air flow path.

In other embodiments, at least a part of the inner wall of the case 110 can be coated with a light reflecting material. For example, a coating layer formed of aluminum or silver, which has high light reflection efficiency with respect to the inner wall at the top of the UV light source 210, can be formed to additionally increase the frequency at which the air flowing through the case 110 along the flow path comes in contact with the UV rays.

Figure 3:
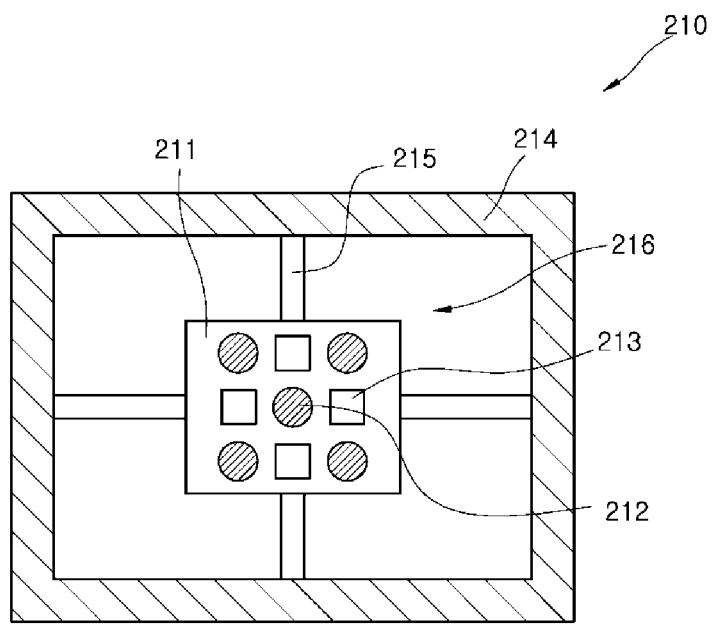
FIG. 3 is a schematic plan view of an exemplary UV light source in accordance with an embodiment of the disclosed technology.

FIG. 3 is a schematic plan top-down view of an exemplary UV light source (e.g., UV light source 210) in accordance with an embodiment of the present disclosure. Referring to FIG. 3, the UV light source 210 can include the PCB 211 having through-holes 216 formed therein. The sterilization UV LEDs 212 and the photocatalyst UV LEDs 213 can be arranged on the PCB 211. As illustrated in FIG. 3, the sterilization UV LEDs 212 and the photocatalyst UV LEDs 213 can be arranged on the PCB 211 so as to cross each other or alternate each other. However, the arrangement is not limited to the one shown in FIG. 3, and the sterilization UV LEDs 212 and the photocatalyst UV LEDs 213 can be arranged in various manners.

The light reflecting structure 214 can be disposed to surround the sterilization UV LEDs 212 and the photocatalyst UV LEDs 213. The inner wall of the light reflecting structure 214 can include a coating layer formed of aluminum or silver, which has high light reflection efficiency. In another embodiment, the light reflecting structure 214 can be formed of aluminum or silver. The light reflecting structure 214 can be structurally supported by the inner wall of the case 110 and a connection member or at least one connection member 215 between the light reflecting structure 214 and the PCB 211. The shape and structure of the connection member 215 can be based on or based at least in part on a variety of publicly-known support structures.

Figure 4:
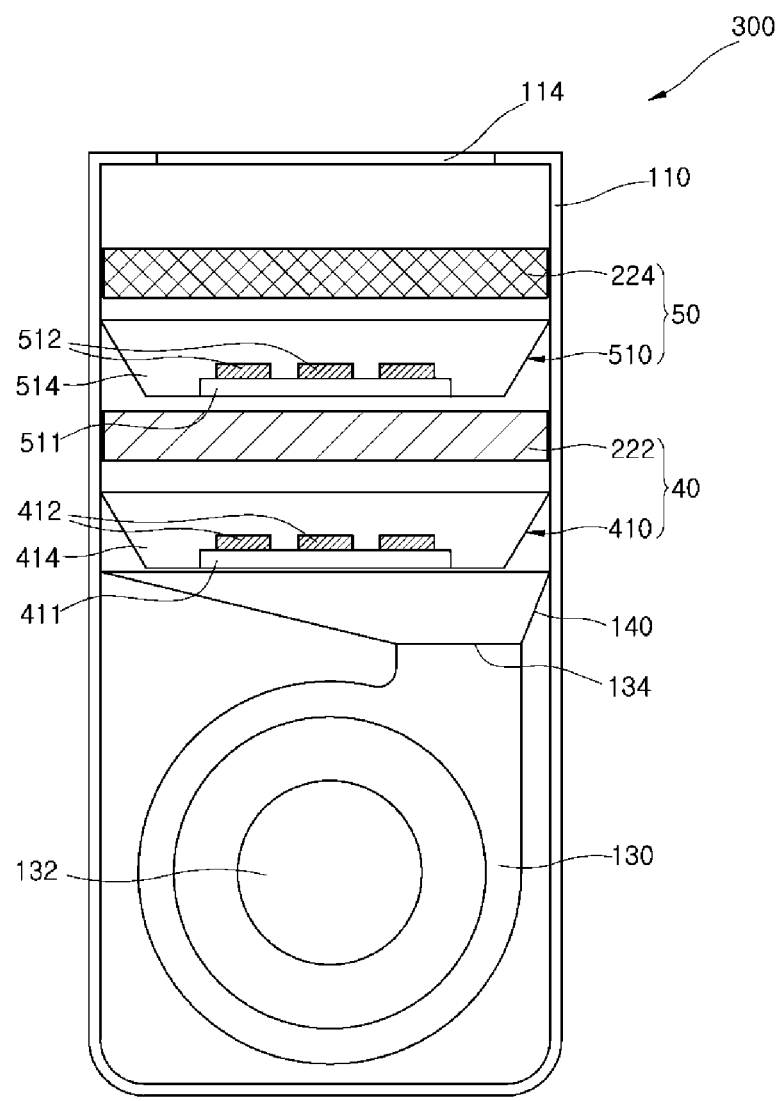
FIG. 4 schematically illustrates an exemplary air purifier in accordance with a second embodiment of the disclosed.

FIG. 4 schematically illustrates an exemplary air purifier in accordance with a second embodiment of the present disclosure. Referring to FIG. 4, the air purifier 300 can have substantially the same configuration as the air purifier 100 in accordance with the first embodiment of the present disclosure, except that the air purifier 300 includes a first air purification unit 40 and a second air purification unit 50, which serve together as the air purification unit. The first air purification unit 40 and the second air purification unit 50 are sequentially arranged along an air flow path to have the second air purification unit 50 disposed over the first air purification unit 40. Thus, the following descriptions will be focused on components that are different from those of the first embodiment of the present disclosure, in order to exclude duplicate descriptions.

Referring to FIG. 4, the first air purification unit 40 can include a first UV light source 410 including sterilization UV LEDs 412 and a collection filter 222. The first UV light source 410 can include a PCB 411 with the sterilization UV LEDs 12 arranged on the PCB 411, and a light reflecting structure 414 disposed to surround the sterilization UV LEDs 412.

The second air purification unit 50 can include a second UV light source 510 including photocatalyst UV LEDs 512 and a photocatalyst filter 224. The second UV light source 510 can include a PCB 511 with the photocatalyst UV LEDs 512 arranged on the PCB 511, and a light reflecting structure 514 disposed to surround the photocatalyst UV LEDs 512.

The first air purification unit 40 can primarily sterilize air flowing through an air duct or a fluid control structure 140, and the second air purification unit 50 can deodorize and sterilize the air having passed through the first air purification unit 40.

In other embodiments, the positions of the first air purification unit 40 and the second air purification unit 50 can be switched to each other. Thus, the second air purification unit 50 can primarily deodorize and sterilize the air flowing through the air duct or fluid control structure 140, and the first air purification unit 40 can sterilize the deodorized and sterilized air having passed through the first air purification unit 40.

Figure 5:
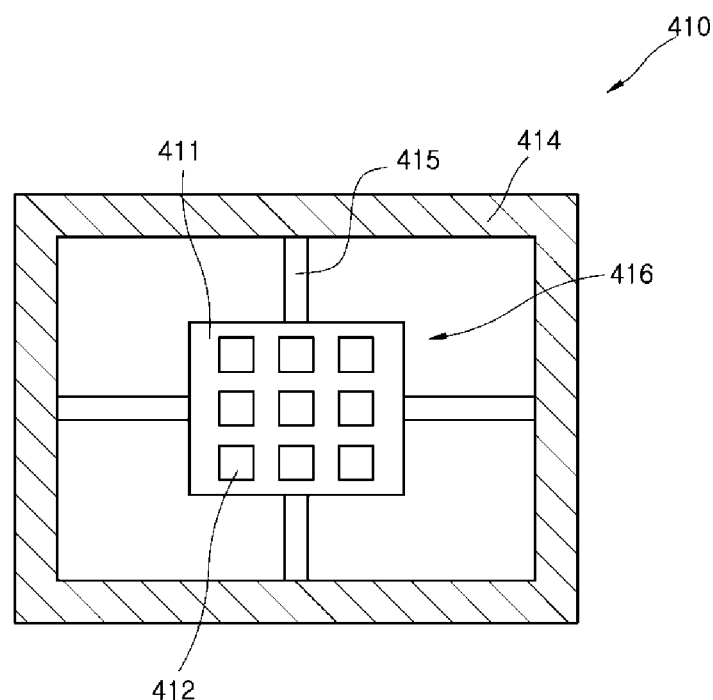
FIG. 5 is a schematic plan view of an exemplary UV light source in accordance with an embodiment of the disclosed technology.

FIG. 5 is a schematic plan top-down view of an exemplary UV light source in accordance with an embodiment of the present disclosure. For example, the UV light source can include the first UV light source 410 described with reference to FIG. 4.

Referring to FIG. 5, the first UV light source 410 can include the PCB 411 having through-holes 416 formed therein. The sterilization UV LEDs 412 can be arranged on the PCB 411. The sterilization UV LEDs 412 can be arranged to form rows as illustrated in FIG. 5. However, the arrangement of the sterilization UV LEDs 412 is not limited to the one shown in FIG. 5, and the sterilization UV LEDs 412 can be arranged in various manners.

The light reflecting structure 414 can be disposed to surround the sterilization UV LEDs 412. The inner wall of the light reflecting structure 414 can include a coating layer formed of aluminum or silver, which has high light reflection efficiency. In another embodiment, the light reflecting structure 414 can be formed of aluminum or silver. The light reflecting structure 414 can be connected to the PCB 411 through a connection member 415, and structurally supported by the PCB 411 and the connection member 415. The shape and structure of the connection member 415 can be implemented in various suitable configurations, including configurations based on or based at least in part on a variety of publicly-known support structures.

In other embodiments, the UV light source can include the second UV light source 510 described with reference to FIG. 4. The second UV light source 510 can have substantially the same configuration as the first light source 410, except that the photocatalyst UV LEDs 512 are mounted on the PCB 511 rather than the sterilization UV LEDs 412.

Figure 6:
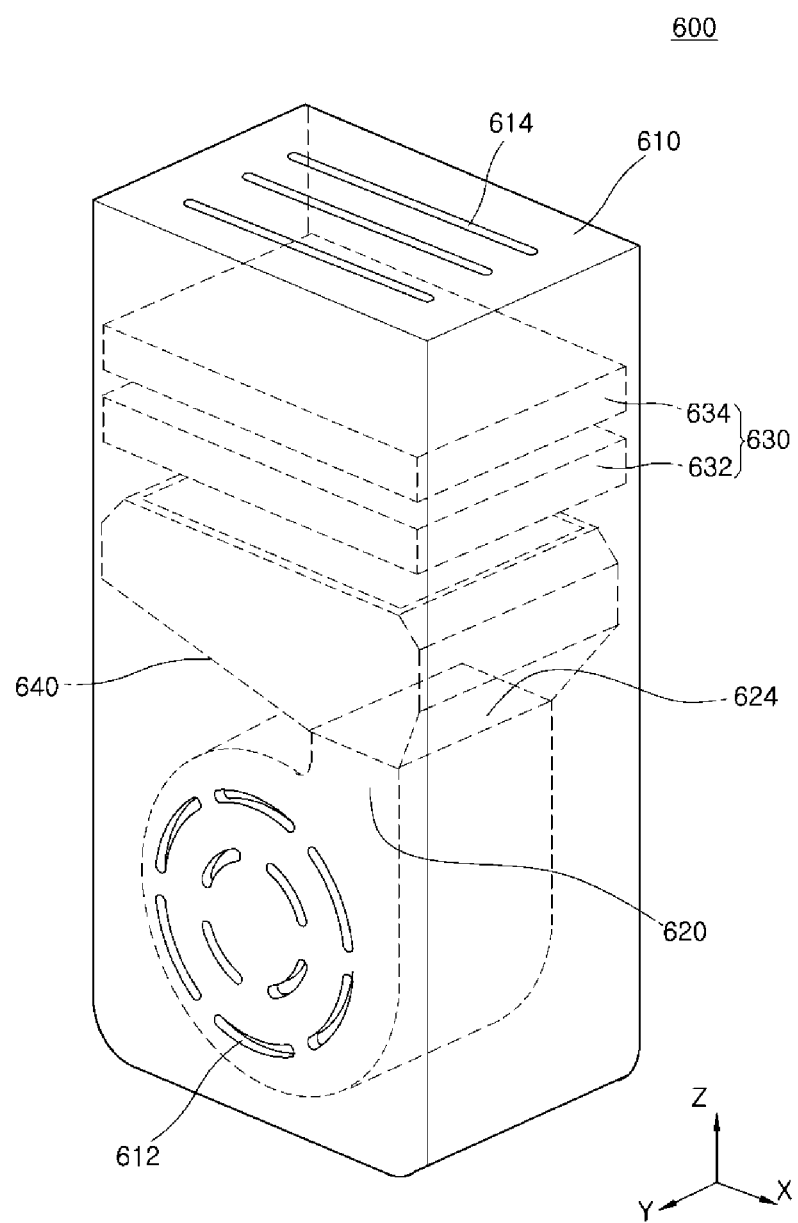
FIG. 6 schematically illustrates an exemplary air purifier in accordance with a third embodiment of the disclosed technology.
Figure 7:
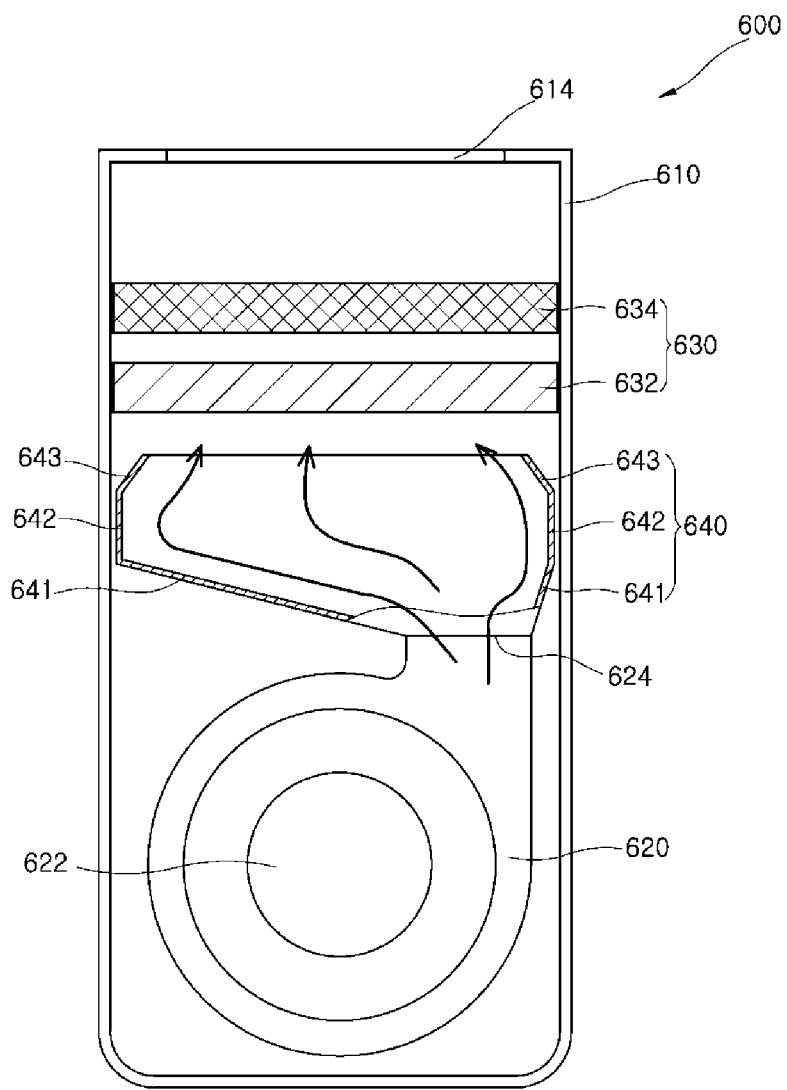
FIG. 7 is a schematic cross-sectional view of the air purifier of FIG. 6.

FIG. 6 schematically illustrates an exemplary air purifier in accordance with a third embodiment of the present disclosure. FIG. 7 is a schematic cross-sectional view of the air purifier of FIG. 6. Referring to FIGS. 6 and 7, the air purifier 600 can include a case 610, a fan 620, a filter unit 630, and other components including a fluid control structure.

The case 610 can include an air inlet 612 and an air outlet 614, and have an air flow path from the air inlet 612 to the air outlet 614. The case 610 can form a frame of the air purifier 600.

The fan 620 can be disposed in the case 610 adjacent to the air inlet 612 to introduce air into an internal space of the case 610. The fan 620 can include a blower fan, for example. The fan 620 can include an inlet 622 adjacent to and substantially aligned with the air inlet 612 to expedite flow of air into the internal space of the case 610. The fan 620 can include an outlet 620 for discharging introduced air towards the filter unit 630. As illustrated in FIGS. 6 and 7, the fan 620 can take air through the air inlet 612 and allow air flow in the direction of a rotation axis of the fan 620, that is, the Y-axis direction. The fan 620 can discharge air flowing in a direction perpendicular to the rotation axis of the fan 620, that is, the Z-axis direction.

When the fan 620 including a blower fan is applied to the case 610, the outlet 624 of the fan 620 can have a smaller cross-sectional area than that of the air flow path formed at least partially by the fluid control structure 640 inside the case 610. Furthermore, a central axis of the outlet 624 of the fan 620 can be positioned at one side from the central axis of the case 610. That is, as illustrated in FIG. 6, the central axis of the outlet 624 of the fan 620 can be separated at a predetermined distance from the central axis of the case 610 in the X- or Y-axis direction.

In the above-described structure, the air discharged from the outlet 624 of the fan 620 can stay around or near the outlet 624 for the fan 620 or flow toward a bottom of the case 610. Furthermore, as the air discharged from the outlet 624 of the fan 620 is focused in one direction, the discharged air can be introduced into the filter unit 630 only through a part of the surface of the filter unit 630.

In order to solve the problem described in the previous paragraph, the fluid control structure or air duct 640 can be disposed between the fan 620 and the filter unit 630. The fluid control structure 640 can control an air flow between the outlet 624 of the fan 620 and the filter unit 630. The fluid control structure 640 can be disposed to change the speed, direction, and density of the air flow around the fluid control structure 640.

In the present embodiment, a fluid duct or air duct 640 serving as the fluid control structure 640 can be disposed to extend from the outlet 624 of the fan 620 toward the inner wall of the case 610. The fluid duct or air duct 640 can control air flow between the outlet 624 of the fan 620 and the filter unit 630.

As illustrated in the drawings, the fluid duct or air duct 640 can include a first duct part 641, a second duct part 643, and a third duct part 642. The first duct part 641 can be extended from the outlet 624 of the fan 620 toward the inner wall of the case 610. The second duct part 643 can be connected to the first duct part 641 through the third duct part 642 and extend in the opposite direction as the first duct part 641 and away from the inner wall of the case 610. The third duct part 642 can be connected to the first and second duct parts 641 and 643 respectively and extend in a direction parallel to the inner wall of the case 610.

The first duct part 641 can serve to prevent or substantially prevent the air discharged from the outlet 624 of the fan 620 from staying around or near the outlet 624 or flowing toward the bottom of the case 610, and spread the discharged air to the internal space of the case 610. The second duct part 643 can be disposed to have a predetermined angle with respect to the longitudinal direction of the case 610. That is, as the second duct part 643 is bent at a predetermined angle toward the inside of the case 610 and away from the inner wall of the case 610, the second duct part 643 can control the air discharged from the outlet 624 of the fan 620 to converge on a central region of the case 610. The third duct part 642 can control the air flow in a state where the air discharged from the outlet 624 of the fan 620 is spread to the entire inner region of the case 610 based on the cross-sectional area of the case 610. In other embodiments, without the third duct part 642, the first duct part 641 can be directly connected to the second duct part 643.

The filter unit 630 can be disposed over the fluid control structure 640. The filter unit 630 can include a first filter 632 and a second filter 634 disposed over the first filter 632. For example, the first filter 632 can be implemented with a deodorization filter, and the second filter 634 can be implemented with a sterilization filter. For another example, the first filter 632 can be implemented with a filtration filter, and the second filter 634 can be implemented with a deodorization filter. As such, the filter unit 630 can include various filters or combination of filters which are sequentially arranged with one above another. The first and second filters 632 and 634 can perform a variety of functions including but not limited to deodorization, sterilization, and filtration.

FIGS. 6 and 7 illustrate that the filter unit 630 includes two filters, that is, the first and second filters 632 and 634. However, the number of filters forming the filter unit 630 is not limited to two.

As the fluid duct is applied as the fluid control structure 640 as described above, the air discharged from the outlet 624 of the fan 620 can be more uniformly introduced into the filter 630. As the flowing air is uniformly spread on a surface area of the filter unit 630, the air purification efficiency of the filter unit 630 can be improved.

In other embodiments, a UV LED unit can be arranged under the filter unit 630. The UV LED unit can have substantially the same configuration as the light source 210 described with reference to FIG. 1. That is, the UV LED unit can include the above-described photocatalyst UV LEDs or the above-described sterilization UV LEDs or both types of UV LEDs.

When the UV LED unit includes the photocatalyst UV LEDs, the filter unit 630 disposed adjacent to or above the UV LED unit can include a photocatalyst filter. When the UV LED unit includes the sterilization UV LEDs, the filter unit 630 can include a collection filter to collect bacteria from the air discharged from the outlet 624 of the fan 620.

Figure 8:
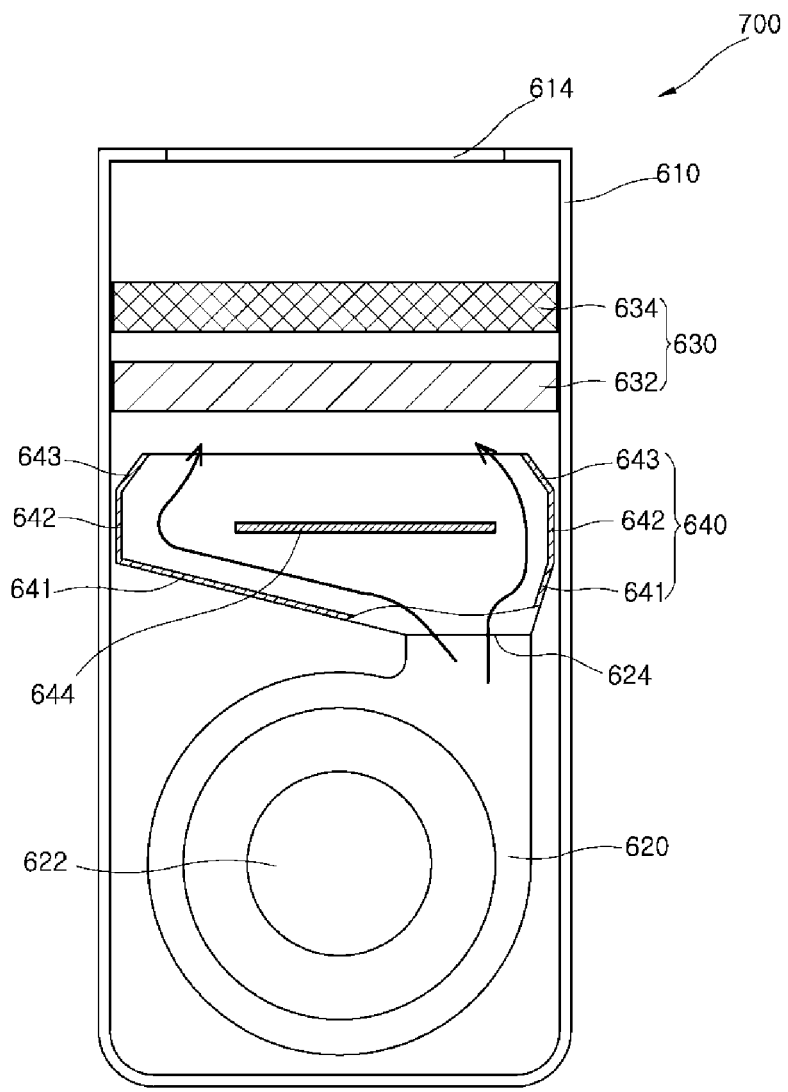
FIG. 8 is a schematic cross-sectional view of an exemplary air purifier in accordance with a fourth embodiment of the disclosed technology.

FIG. 8 is a schematic cross-sectional view of an exemplary air purifier in accordance with a fourth embodiment of the present disclosure. Referring to FIG. 8, an air purifier 700 can have substantially the same configuration as the air purifier 600 described with reference to FIGS. 6 and 7, except that the air purifier 700 additionally includes a plate-shaped structure 644 serving as a fluid control structure. Thus, the following descriptions will be focused on components that are different from the air purifier 600, in order to exclude duplicate descriptions.

The plate-shaped structure 644 can be disposed in the fluid duct 640 as shown in FIG. 8. The plate-shaped structure 644 can have one surface disposed to face the air flow path direction so as to interfere with air flow within the case 610. For example, the one surface of the plate-shaped structure 644 can be disposed in a direction which is substantially perpendicular to the flow path direction of the air discharged from the outlet 624 of the fan 620. For another example, the one surface of the plate-shaped structure 644 can be disposed to have a slope at a predetermined angle with respect to the flow path direction of the air discharged from the outlet 624 of the fan 620.

As illustrated in FIG. 8, the plate-shaped structure 644 can interfere with the air discharged from the outlet 624 of the fan 620, and an air flow can be formed to avoid the plate-shaped structure 644. The plate-shaped structure 644 and the fluid duct 640 can be applied to properly control the flow of air flowing toward the filter unit 630. That is, the plated-shaped structure 644 can prevent the concentration of air flow on a specific region of the filter unit 630, caused by the structure of the fan 620. Furthermore, while the air passes through the plate-shaped structure 644, the flow velocity of the air can be slowed to increase the time during which the air reacts with the filter unit 630.

The configuration and arrangement of the plate-shaped structure 644 and the fluid duct 640 can be determined through a structure of the outlet 624 of the fan 620, a discharge performance of the fan 620 (that is, the discharge flow rate and the discharge flow velocity), and an internal structure of the case 610.

In other embodiments, a UV LED unit can be disposed under or below the filter unit 630. The UV LED unit can have substantially the same configuration as the UV light source 210 described with reference to FIG. 1. That is, the UV LED unit can include the above-described photocatalyst UV LEDs or the above-described sterilization UV LEDs or both types of UV LEDs.

When the UV LED unit includes the photocatalyst UV LEDs, the filter unit 630 disposed adjacent to or above the UV LED unit can include a photocatalyst filter. When the UV LED unit includes the sterilization LED units, the filter unit 630 can include a collection filter to collect bacteria.

Figure 9A:
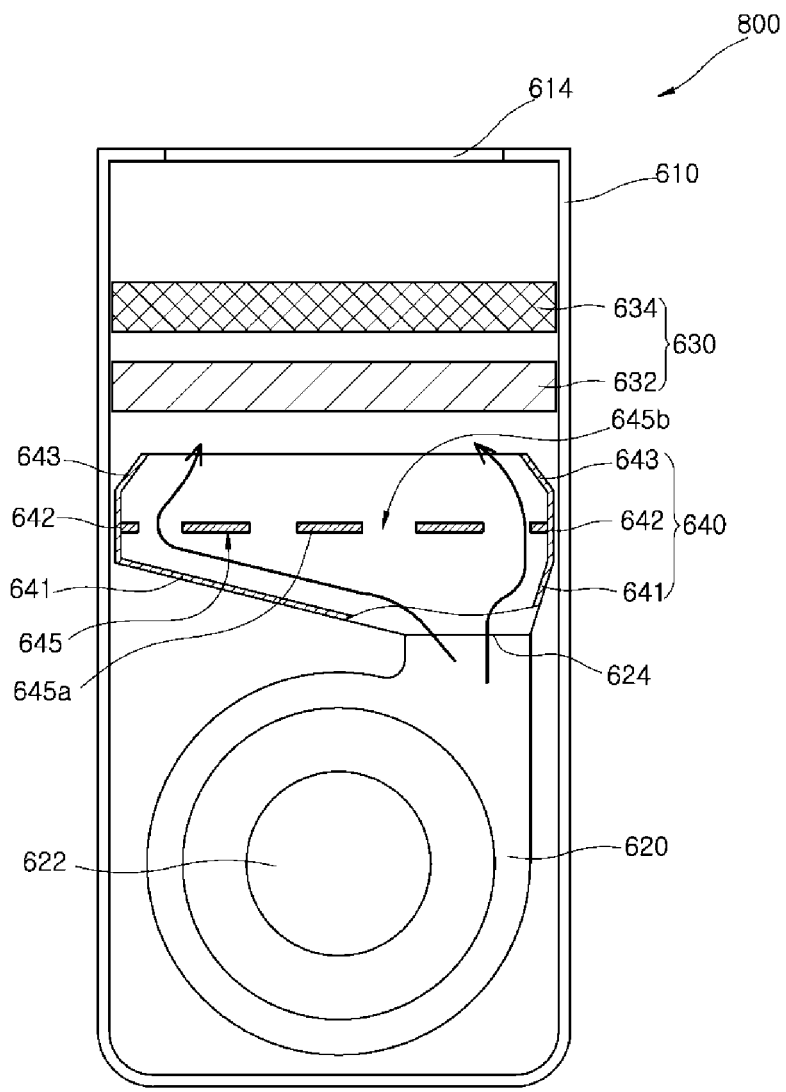
FIG. 9A is a schematic cross-sectional view of an exemplary air purifier in accordance with a fifth embodiment of the disclosed technology.
Figure 9B:
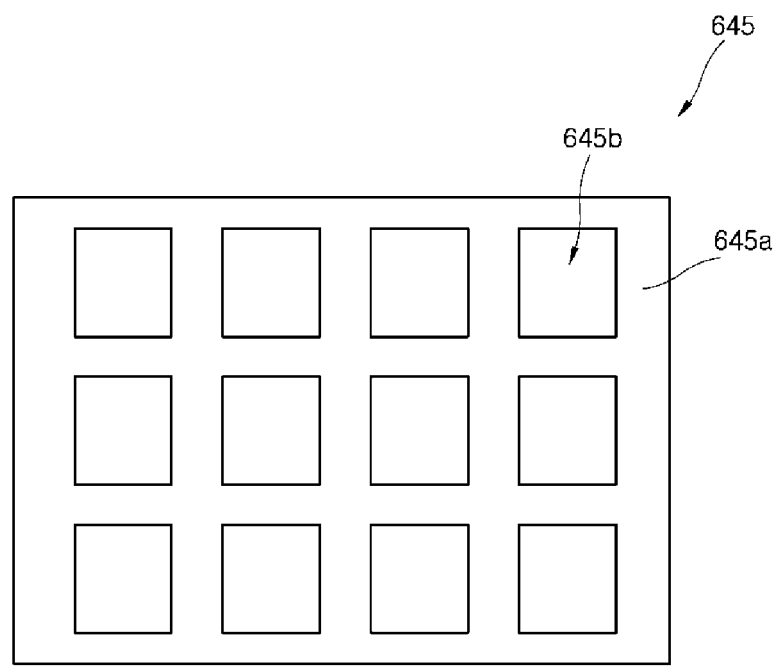
FIG. 9B is a schematic plan view of an exemplary fluid control structure applied to the air purifier of FIG. 9A.

FIG. 9A is a schematic cross-sectional view of an exemplary air purifier in accordance with a fifth embodiment of the present disclosure. FIG. 9B is a schematic plan view of an exemplary fluid control structure applied to the air purifier of FIG. 9A. Referring to FIGS. 9A and 9B, the air purifier 800 can have substantially the same configuration as the air purifier 600 described with reference to FIGS. 6 and 7, except that the air purifier 800 additionally includes a plate-shaped structure 645 having through-holes formed on the plate-shaped structure 645 and serving as a fluid control structure or a part of a fluid control structure. Furthermore, the plate-shaped structure 645 can have substantially the same configuration as the plate-shaped structure 644 of the air purifier 700 described with reference to FIG. 8, except that the plate-shaped structure 645 has through-holes formed on the plate-shaped structure 645. Thus, the following descriptions will be focused on components that are different from the plate-shaped structure 644, in order to exclude duplicate descriptions.

Referring to FIG. 9B, the plate-shaped structure 645 can include a frame part 645a having through-holes 645b formed on the frame part 645a. The frame part 645a can serve to interfere with air flows. The air flowing to the plate-shaped structure 645 can pass through the through-holes 645b of the plate-shaped structure 645. The through-holes 645b of the plate-shaped structure 645 can be formed in a proper shape to control the flow of air flowing toward the filter unit 630. That is, the plate-shaped structure 645 can prevent the concentration of the air flow on a specific region of the filter unit 630, caused by the structure of the fan 620. Furthermore, while the air passes through the plate-shaped structure 645, the flow velocity of the air flowing through the plate-structure 645 can be slowed to increase the time during which the air reacts with the filter unit 630. The size and arrangement of the through-holes 645b can be determined through the structure of the outlet 624 of the fan 620, the discharge performance (that is, discharge flow rate and discharge flow velocity) of the fan 620, and the internal structure of the case 610.

In other embodiments, a UV LED unit can be disposed under the filter unit 630. The UV LED unit can have substantially the same configuration as the UV light source 210 described with reference to FIG. 1. That is, the UV LED unit can include the above-described photocatalyst UV LEDs or the above-described sterilization UV LEDs or both types of UV LEDs.

When the UV LED unit includes the photocatalyst UV LEDs, the filter unit 630 disposed adjacent to or above the UV LED unit can include a photocatalyst filter. When the UV LED unit includes the sterilization LED units, the filter unit 630 can include a collection filter to collect bacteria.

Figure 10B:
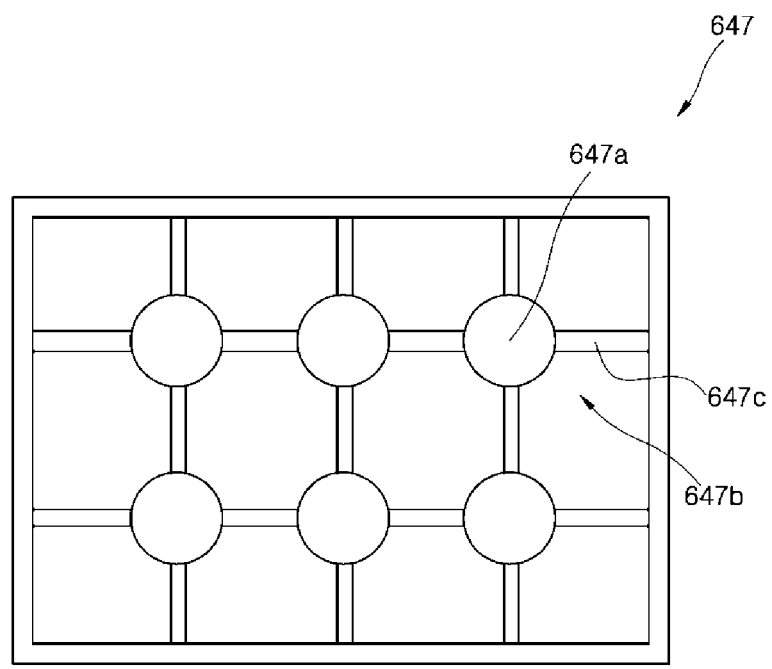
FIG. 10B is a schematic plan view of an exemplary fluid control structure applied to the air purifier of FIG. 10A.

FIG. 10A is a schematic cross-sectional view of an exemplary air purifier in accordance with a sixth embodiment of the present disclosure. FIG. 10B is a schematic plan top-down view of an exemplary fluid control structure applied to the air purifier of FIG. 10A.

Referring to FIGS. 10A and 10B, the air purifier 900 can have substantially the same configuration as the air purifier 600 described with reference to FIGS. 6 and 7, except that the air purifier 900 additionally includes a spherical structure 647 serving as a fluid control structure. Thus, the following descriptions will be focused on components different from air purifier 600, in order to exclude duplicate descriptions.

The spherical structure 647 can generate a vortex through a pressure difference when air flows on the outer circumferential surface of the spherical structure 647. Such a vortex can serve to mix the air flowing through the fluid control structure such that the air reaches the filter unit 630 in a more uniform state.

Referring to FIG. 10B, the spherical structure 647 can include spherical structure parts 647a and a frame part 647c for connecting the spherical structure parts 647a, and the frame part 647c can have through-holes 647b formed on the frame part 647c. The spherical structure parts 647a can have such a size as to generate vortexes around the structure parts 647a. The size and arrangement of the spherical structure parts 647a can be determined through a structure of the outlet 624 of the fan 620, a discharge performance (that is, discharge flow rate and discharge flow velocity) of the fan 620, and an internal structure of the case 610.

In other embodiments, a UV LED unit can be disposed under the filter unit 630. The UV LED unit can have substantially the same configuration as the UV light source 210 described with reference to FIG. 1. That is, the UV LED unit can include the above-described photocatalyst UV LEDs or the above-described sterilization UV LEDs or both types of UV LEDs.

When the UV LED unit includes the photocatalyst UV LEDs, the filter unit 630 disposed adjacent to or above the UV LED unit can include a photocatalyst filter. When the UV LED unit includes the sterilization LEDs, the filter unit 630 can include a collection filter to collect bacteria from the air discharged from the outlet 624 of the fan 620 and flowing through the filter unit 630.

Figure 11A:
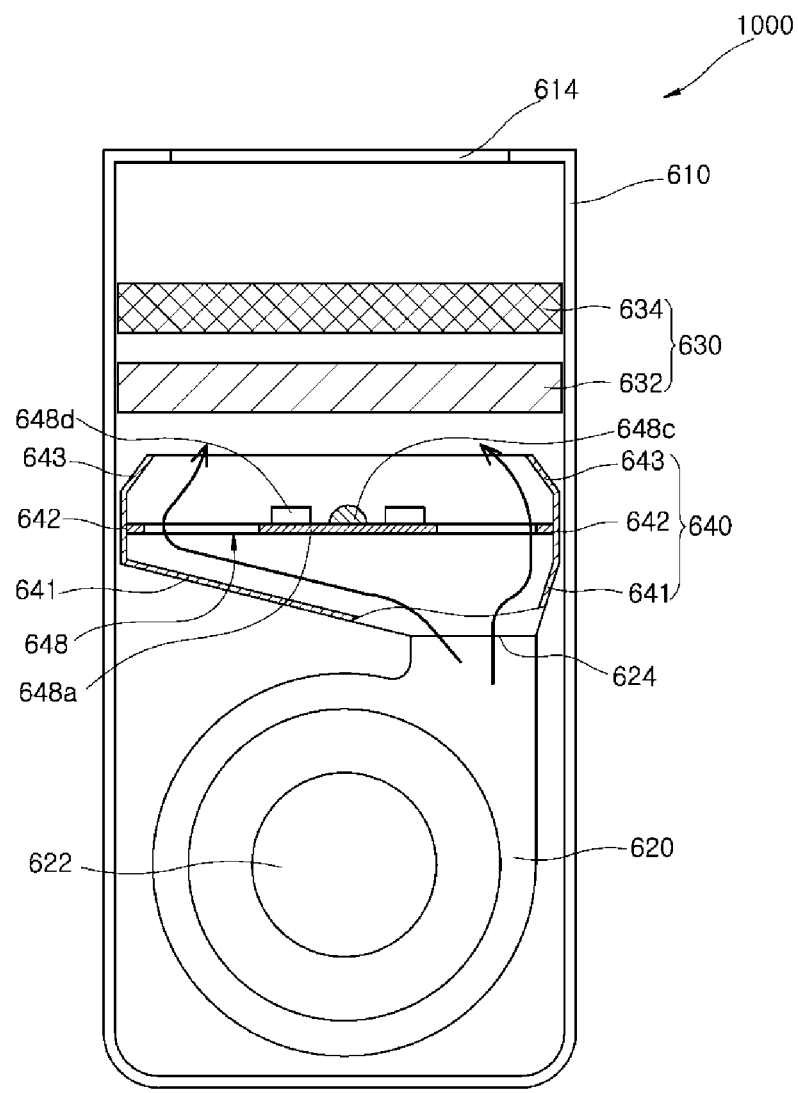
FIG. 11A is a schematic cross-sectional view of an exemplary air purifier in accordance with a seventh embodiment of the disclosed technology.
Figure 11B:
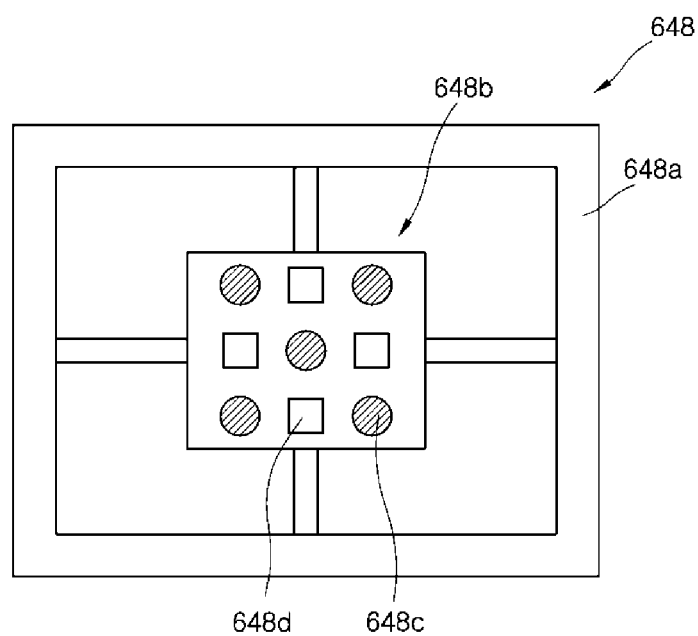
FIG. 11B is a schematic plan view of an exemplary UV LED unit applied as a fluid control structure of the air purifier of FIG. 11A.

FIG. 11A is a schematic cross-sectional view of an exemplary air purifier in accordance with a seventh embodiment of the present disclosure. FIG. 11B is a schematic plan top-down view of a UV LED unit applied as a fluid control structure of the air purifier of FIG. 11A.

Referring to FIGS. 11A and 11B, the air purifier 1000 can have substantially the same configuration as the air purifier 600 described with reference to FIGS. 6 and 7, except that a UV LED unit 648 is applied as a fluid control structure. Thus, the following descriptions will be focused on components that are different from the air purifier 600, in order to exclude duplicate descriptions.

The UV LED unit 648 can include a PCB 648a having through-holes 648b formed on the PCB 648a and UV LEDs 648c and 648d arranged on the PCB 648a.

In accordance with the seventh embodiment, the UV LEDs 648c and 648d can react with the filter unit 630 to perform a sterilization or deodorization action. For example, when the UV LED 648c is a photocatalyst LED 648c, the first or second filter of the filter unit 630 can include a photocatalyst filter. The photocatalyst filter can emit UV rays with a wavelength of about 700 to 800 nm such that the UV rays react with the photocatalyst medium of the photocatalyst filter. Through the photocatalytic reaction, hydroxyl radicals having strong oxidizing power can be generated to perform a sterilization or deodorization action. For another example, when the UV LED 648c is a sterilization LED, the first or second filter of the filter unit 630 can include a collection filter. The collection filter can collect bacteria in the flowing air discharged from the outlet 624, and the sterilization LED can sterilize the collected bacteria by emitting UV rays with a wavelength of about 200 to 700 nm onto the bacteria. In other embodiments, the UV LEDs 648c and 648d can be implemented with only photocatalyst LEDs or sterilization LEDs.

In the present embodiment, the PCB 648a having the UV LEDs 648c and 648d mounted on the PCB 648a can be applied as the fluid control structure. The PCB 648a can pass air flowing through the through-holes 648b, and the other parts of the PCB 648a excluding the through-holes 648b can be used to interfere with the air flow. As such, the PCB 648a having the through-holes 648b formed on the PCB 648a can be applied to prevent or substantially prevent the concentration of air flow on a specific region of the filter unit 630, which is caused by the structure of the fan 630. While the air passes through the PCB 648a, the flow velocity of the air can be slowed to increase the time during which the air reacts with the filter unit 630. At this time, the size and arrangement of the through-holes 648b can be determined through the structure of the outlet 624 of the fan 620, the discharge performance (that is, discharge flow rate and discharge flow velocity) of the fan 620, and the internal structure of the case 610.

In other embodiments, a structure capable of slowing the flow velocity of air can be additionally disposed under the filter unit 630. Such a structure can include a cabin filter having a large pressure difference between front and rear stages, for example. As the air flow is slowed by the cabin filter, the time during which the air flow stays in the filter unit 630 can be sufficiently secured to increase the sterilization or deodorization efficiency of the filter unit 630.

Figure 12:
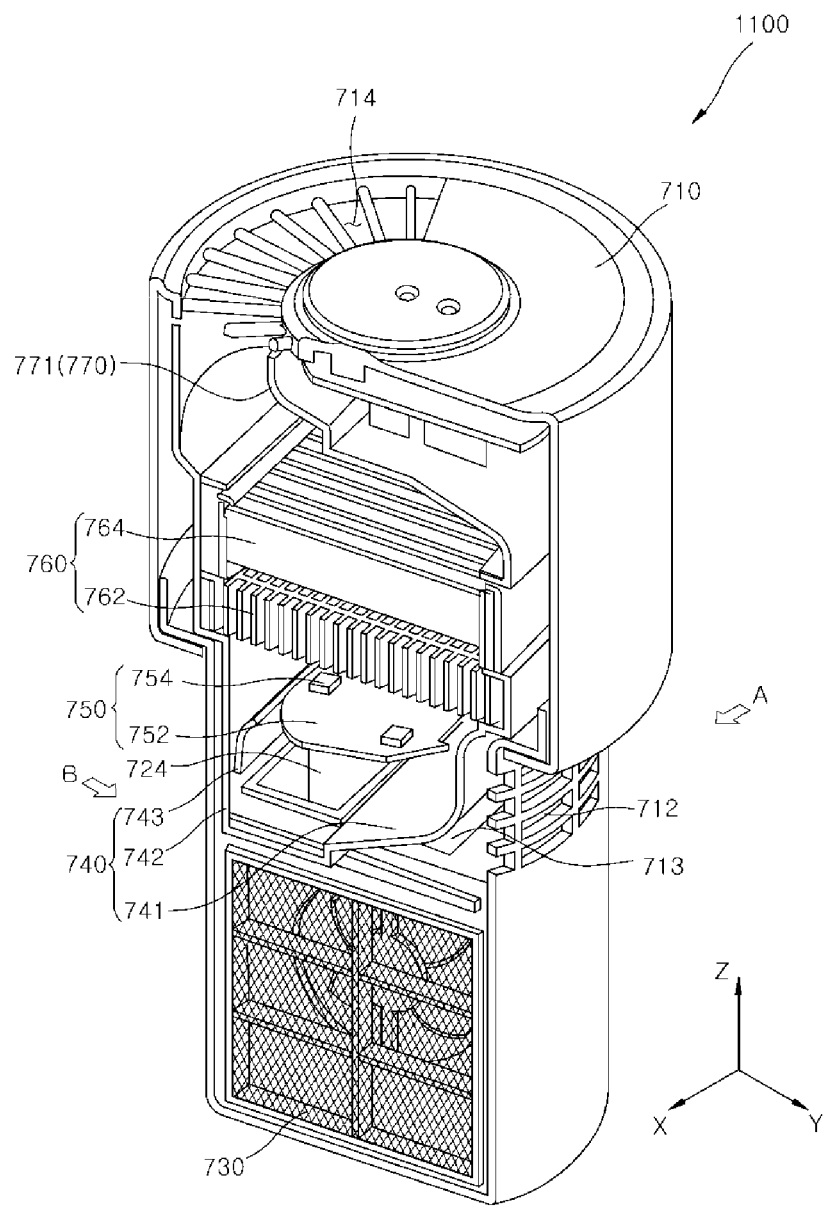
FIG. 12 is a schematic cross-sectional view of an exemplary air purifier in accordance with an eighth embodiment of the disclosed technology.
Figure 13A:
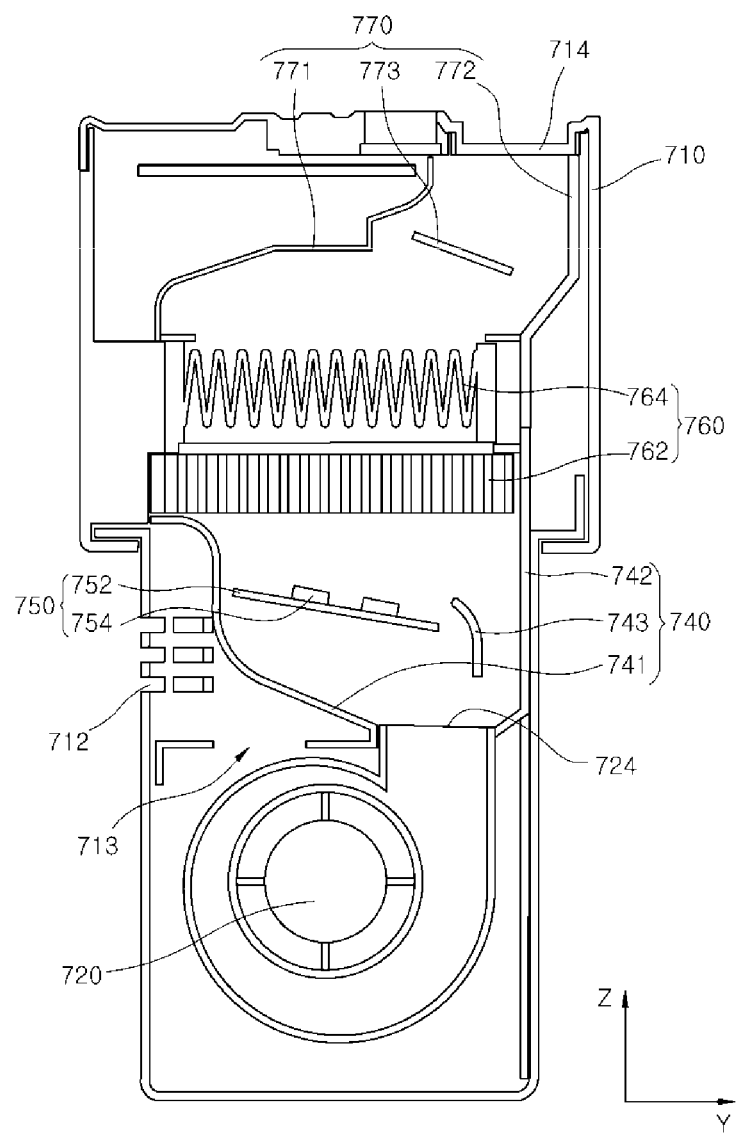
FIG. 13A is a cross-sectional view of the air purifier of FIG. 12, seen from a direction A.
Figure 13B:
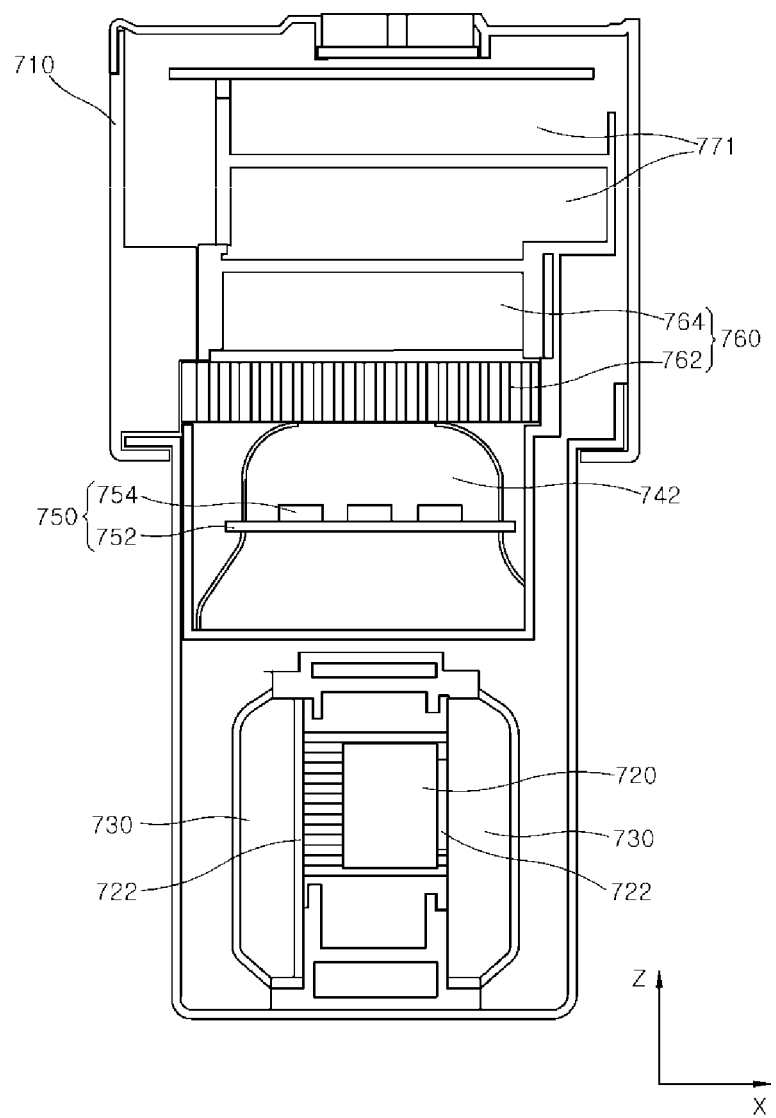
FIG. 13B is a cross-sectional view of the air purifier of FIG. 12, seen from a direction B.

FIG. 12 is a schematic cross-sectional view of an exemplary air purifier in accordance with an eighth embodiment of the present disclosure. FIG. 13A is a cross-sectional view of the air purifier of FIG. 12, seen from a direction A, an exemplary direction. FIG. 13B is a cross-sectional view of the air purifier of FIG. 12, seen from a direction B, another exemplary direction different from direction A.

Referring to FIGS. 12, 13a, and 13b, the air purifier 1100 can include a case 710 having a first air inlet 712 and an air outlet 714. The case 710 can include a frame forming an exterior structure of the air purifier 1100. Referring to FIGS. 12 and 13A, the first air inlet 712 can be formed at a side of the case 710, and the air introduced into the case 710 through the first air inlet 712 can be introduced to a fan 720 through a second air inlet 713. The fan 720 can include a blower fan, for example.

The air introduced through the second air inlet 713 can be introduced into a fan inlet 722 through the first filter unit 730. The first filter unit 730 can include a variety of functional filtration filters such as a dust filter, a collection filter, and a carbon filter, for example. The air introduced into the fan inlet 722 can be discharged through an outlet 724 according to the operation of the fan 720.

The central axis of the outlet 724 of the fan 720 can be positioned at one side from the central axis of the case 710. As illustrated in FIG. 13A, the central axis of the outlet 724 of the fan 720 can be separated at a predetermined distance from the central axis of the case 710 in the Y-axis direction.

The first fluid control structure 740 can be disposed at the top of the outlet 724. The first fluid control structure 740 can include a first duct inner wall 741 and a second duct inner wall 742. The first duct inner wall 741 and the second duct inner wall 742 can have an asymmetrical shape with each other with respect to a central axis of the air duct along the height direction of the case 710. For example, the first duct inner wall part 741 and the second duct inner wall 742 can have various shapes such as a curve and a straight line. Furthermore, the first and second inner walls 741 and 742 can have substantially the same shape as the fluid control structure 640 described with reference to FIGS. 6 and 7.

The first fluid control structure 740 can further include a control structure 743 within the duct. The control structure 743 can include the plate-shaped structure 644 described with reference to FIG. 8, the plate-shaped structure 645 having the through-holes and described with reference to FIGS. 9A and 9B, or the plate-shaped structure 647 described with reference to FIGS. 10A and 10B. The control structure 743 can have various shapes such as a straight line and a curve, for example. As described above, the first fluid control structure 740 can control the flow of air which is discharged from the outlet 724 and flows into the filter unit 760.

A UV LED unit 750 can be disposed adjacent to the first fluid control structure 740. When the first fluid control structure 740 has a duct shape, the UV LED unit 750 can be disposed in the first fluid control structure 740 serving as the duct or at least a part of the duct.

The UV LED unit 750 can include a PCB 752 and UV LEDs 754 mounted on the PCB 752. The UV LEDs 754 can include the above-described sterilizing LEDs or the above-described photocatalytic LEDs or both.

The filter unit 760 can be disposed over the UV LED unit 750. As illustrated in the drawings, the filter unit 760 can include a photocatalyst filter 762 and a collection filter 764. The photocatalyst filter 762 can function with the photocatalyst LEDs of the UV LED unit 750. Furthermore, the collection filter 764 can function with the sterilizing LEDs.

As illustrated in FIG. 13A, the PCB 752 of the UV LED unit 750 can be inclined at a predetermined angle with respect to the filter unit 760. That is, the surface of the PCB 752 can be disposed so as not to be parallel to the surface of the filter unit 760. Thus, the frequency at which light emitted from the UV LEDs 754 collides with a mesh of the filter unit 760 can be increased to improve the efficiency of the photocatalytic reaction with a photocatalytic material applied on the mesh or the sterilization action for bacteria collected in the mesh.

A second fluid control structure 770 can be disposed over the filter unit 760. The second fluid control structure 770 can be disposed to extend to the air outlet 714. The second fluid control structure 770 can include an air or fluid duct having a first duct inner wall 771 and a second duct inner wall 772. The first duct inner wall 771 and the second duct inner wall 772 can have an asymmetrical shape with each other with respect to the central axis of the duct along the height direction of the case 710. For example, the first duct inner wall 771 and the second duct inner wall 772 can have various shapes such as a straight line and a curve. Furthermore, the first duct inner wall 771 and the second duct inner wall 772 can have substantially the same shape as the fluid control structure 640 described with reference to FIGS. 6 and 7.

The second fluid control structure 770 can further include a control structure 773 within the duct. The control structure 773 can include the plate-shaped structure 644 described with reference to FIG. 8, the plate-shaped structure 645 having the through-holes and described with reference to FIGS. 9A and 9B, or the spherical structure 647 described with reference to FIGS. 10A and 10B. The control structure part 772 can have various three-dimensional shapes such as a straight line and a curve. The second fluid control structure 770 can control the flow of air which is discharged through the filter unit 760 and flows into the air outlet 714.

Only a few embodiments, implementations and examples are described and other embodiments and implementations, and various enhancements and variations can be made based on what is described and illustrated in this document.

What is claimed is:

1. An air purifier comprising:
a case having a first surface, a second surface opposing the first surface, and a sidewall connecting the first surface and the second surface, an air inlet and an air outlet;
a fan disposed inside the case and adjacent to the air inlet;
an ultraviolet (UV) light emitting diode (LED) unit and a filter unit arranged inside the case and over the fan along a flow path of air; and
a fluid control structure disposed inside the case and positioned between the fan and the UV LED unit, the fluid control structure including a first duct part coupled to an outlet of the fan and having an increasing width along the flow path of air and a third duct part extending from the first duct part in a direction parallel to the sidewall of the case,
wherein the fluid control structure controls an air flow along the flow path of air between the outlet of the fan and the filter unit.

2. The air purifier of claim 1, wherein the outlet of the fan has a smaller cross-sectional area than that of the filter unit of the case.

3. The air purifier of claim 1, wherein the fluid control structure further comprises:
a second duct part disposed closer to the filter unit than the fan and extended in a direction away from the sidewall of the case.

4. The air purifier of claim 3, wherein the second duct part has a predetermined angle with respect to a longitudinal direction of the case.

5. The air purifier of claim 1, wherein the fluid control structure comprises a plate-shaped structure having a surface disposed to face the flow path of the air within the case.

6. The air purifier of claim 1, further comprising a light reflecting structure disposed to surround the UV LED unit.

7. The air purifier of claim 1, wherein the UV LED unit is structured to emit UV light within a wavelength range that can directly sterilize air by illuminating the air.

8. The air purifier of claim 1, wherein:
the filter unit includes a photocatalyst material that reacts to UV light to cause photocatalytic reactions that sterilize the air; and
the UV LED unit emits UV light within a wavelength range that can cause photocatalytic reactions in the photocatalyst material, and is configured to direct the UV light onto the photocatalyst material.

9. The air purifier of claim 1, further comprising an air purification unit disposed over the fan to receive and purify air discharged from the outlet of the fan.

10. The air purifier of claim 1, wherein the UV LED unit includes UV LEDs that emit UV light at different UV spectral ranges from each other.

11. The air purifier of claim 1, wherein the UV LED unit includes an UV LED emitting UV light within a wavelength range from 200 nm to 300 nm.

12. The air purifier of claim 1, wherein the UV LED unit includes an UV LED emitting UV light within a wavelength range from 300 nm to 400 nm.

13. The air purifier of claim 1, wherein the filter unit includes titanium oxide ($TiO_2$), zinc oxide (ZnO), tungsten oxide ($WO_3$), or zirconium oxide ($ZrO_2$).

14. The air purifier of claim 1, wherein the fluid control structure includes a first duct inner wall and a second duct inner wall that are asymmetrical with respect to a central axis of the fluid control structure.

15. The air purifier of claim 1, wherein the fluid control structure includes a portion that faces the filter unit, the portion has a width covering the filter unit.

16. The air purifier of claim 1, wherein the air inlet is located in the sidewall and the air outlet is located in one of the first surface and the second surface.

17. The air purifier of claim 1, further comprising:
an additional fluid control structure disposed over the filter unit and extended to the air outlet, the additional fluid control structure having a decreasing width along the direction parallel to the sidewall of the case.

18. The air purifier of claim 1, wherein the outlet of the fan is positioned closer to the sidewall than a central axis of the case.

* * * * *